(12) United States Patent
Sato et al.

(10) Patent No.: US 9,084,560 B2
(45) Date of Patent: Jul. 21, 2015

(54) PHOTOACOUSTIC APPARATUS AND METHOD FOR CONTROLLING THE SAME

(75) Inventors: Akira Sato, Kawasaki (JP); Yoshiaki Sudo, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 631 days.

(21) Appl. No.: 13/514,955

(22) PCT Filed: Nov. 26, 2010

(86) PCT No.: PCT/JP2010/071748
§ 371 (c)(1),
(2), (4) Date: Jun. 8, 2012

(87) PCT Pub. No.: WO2011/070985
PCT Pub. Date: Jun. 16, 2011

(65) Prior Publication Data
US 2013/0031982 A1   Feb. 7, 2013

(30) Foreign Application Priority Data

Dec. 11, 2009   (JP) ................... 2009-282287

(51) Int. Cl.
*A61B 5/00* (2006.01)
*A61B 8/08* (2006.01)

(52) U.S. Cl.
CPC .............. *A61B 8/08* (2013.01); *A61B 5/0095* (2013.01)

(58) Field of Classification Search
CPC ......... A61B 5/0095; A61B 8/08; A61B 8/587
See application file for complete search history.

(56) References Cited

U.S. PATENT DOCUMENTS 4,385,634 A   5/1983   Bowen
5,840,023 A   11/1998  Oraevsky et al.

FOREIGN PATENT DOCUMENTS

| EP | 1743576 A1 | 1/2007 |
|---|---|---|
| JP | 2008253482 A | 10/2008 |
| JP | 2009136324 A | 6/2009 |
| JP | 2009142321 A | 7/2009 |
| WO | 9727801 A1 | 8/1997 |
| WO | 2004062491 A1 | 7/2004 |
| WO | 2008103982 A2 | 8/2008 |

OTHER PUBLICATIONS

Razansky et al."Hybrid Photoacoustic Fluoresence Molecular Tomography Using Finite-Element-Based Inversion" Medical Physics, vol. 34, No. 11, Nov. 2007, pp. 4293-4301.

*Primary Examiner* — Michael Rozanski
(74) *Attorney, Agent, or Firm* — Canon USA Inc. IP Division

(57) ABSTRACT

Provided is a photoacoustic apparatus capable of recognizing light quantity unevenness, which occurs on a surface of an analyte, and decreasing image unevenness resulted from the light quantity unevenness.
A photoacoustic apparatus includes a light source configured to irradiate an analyte with light; an optical system configured to guide the light from the light source to the analyte; a detecting unit including a receiving element configured to receive an acoustic wave generated in the analyte by the light; a signal processing unit configured to acquire information about the inside of the analyte from a detected signal acquired from the detecting unit; an optical absorber configured to absorb the light from the light source; and a calculation unit configured to calculate an irradiation intensity distribution of the light on the basis of a detected signal acquired when the receiving element receives the acoustic wave generated from the optical absorber.

20 Claims, 9 Drawing Sheets

PHOTOACOUSTIC APPARATUS AND METHOD FOR CONTROLLING THE SAME

TECHNICAL FIELD

The present invention relates to a photoacoustic apparatus that receives a photoacoustic wave generated when an analyte is irradiated with light.

BACKGROUND ART

A study on an optical imaging apparatus has been promoted in medical fields. The optical imaging apparatus irradiates a living body with light from a light source such as a laser, and forms an image of information about the inside of the living body acquired on the basis of the incident light. The optical imaging technique includes photoacoustic tomography (PAT). The photoacoustic tomography irradiates a living body with pulsed light generated from a light source and detects an acoustic wave generated from a living tissue absorbing the energy of the pulsed light propagating through and diffused in the living body (Patent Literature 1). More specifically, the technique uses a difference in absorptance of light energy between a detection portion such as a tumor and the other tissues, and receives by receiving elements an elastic wave that is generated when the detection portion absorbs the light energy and instantly expands. By analyzing the detected signal, the information can be used in measurement for an optical characteristic distribution in a living body, and more particularly, quantitative measurement for a specific substance in the analyte, for example, glucose or hemoglobin contained in the blood. Hence, the information can be used for specifying the position of a malignant tumor accompanying with the growth of new blood vessels. In particular, a light-energy absorption-density distribution can be obtained.

With PAT, an acoustic wave that is generated as the result of absorption of light in a local detection portion of an analyte is measured, and hence local light absorption information can be acquired. A model is described below, in which an analyte is fixed to a flat plate, a light irradiation region with laser light is two-dimensionally set on a surface of the analyte, and the light irradiation region is sufficiently large for an imaging area. When d is a distance from a light irradiation point to the detection portion, an initial sound pressure P of the acoustic wave generated at the detection portion is expressed as follows:

$$P(d) = \Gamma \mu_a(d) \Phi(d) \quad \text{Expression (1),}$$

where $\gamma$ is a Gruneisen coefficient (heat-acoustic conversion efficiency), $\mu_a(d)$ is an absorption coefficient at the position of the distance d, and $\Phi(d)$ is a light intensity at the position of the distance d. The Gruneisen coefficient $\Gamma$, which is an elasticity value, is obtained by dividing a product of a thermal expansion coefficient beta and the square of the sound speed c, by a specific heat at constant pressure Cp. In general, the Gruneisen coefficient $\Gamma$ is a substantially constant value. Hence, if a change in sound pressure P, which is the magnitude of the acoustic wave, is measured by time division, the product of $\mu_a$ and $\Phi$, that is, the light-energy absorption-density distribution H can be obtained. Then, by dividing H by the local light intensity $\Phi(d)$, $\mu_a(d)$ can be obtained.

Also, it is assumed that $\Phi_0$ is a light quantity of pulsed light that is emitted on the surface of the analyte. Light is exponentially attenuated in the analyte by absorption and scattering as the light propagates away from the surface. That is, the local light intensity $\Phi(d)$ can be expressed as follows:

$$\Phi(d) = \Phi_0 \cdot \exp(-\mu_{eff} d) \quad \text{Expression (2),}$$

where $\mu_{eff}$ is an average equivalent attenuation coefficient of the analyte. From Expressions (2) and (1), Expression (3) is established as follows:

$$P(d) = \Gamma \mu_a(d) \Phi_0 \cdot \exp(-\mu_{eff} d) \quad \text{Expression (3).}$$

CITATION LIST

Patent Literature

PTL 1 U.S. Pat. No. 5,840,023

SUMMARY OF INVENTION

Technical Problem

In laser ultrasonic measurement, strong laser light is guided to an optical system, and a surface of an analyte is two-dimensionally irradiated with the laser light as diffused laser light, to cause the analyte to generate an ultrasonic wave. When the laser light is guided to the optical system, irradiation unevenness, in which the intensity of the laser light may be unevenly distributed, may occur. The major factor of the irradiation unevenness is that when a reflection mirror or the like is used as a light guide unit, very small irregularities of a reflection surface of the mirror may unevenly reflect the laser light, resulting in appearance of speckles. In contrast, if the reflection mirror is not used but an optical fiber is used as a light guide unit for the laser light, the speckles do not appear at the reflection surface. However, if a light path is determined with the optical fiber, an incident angle and an exit angle of the light to and from the optical fiber have to be precisely controlled to finally obtain a uniform irradiation distribution. If a light axis of incident light to the optical fiber is deviated from a light axis that is expected when the optical fiber is designed, when the light is exited from the optical fiber, irradiation unevenness may occur.

That is, the value $\Phi_0$ may vary depending on the position on the surface of the analyte. The irradiation intensity unevenness within the light irradiation region on the surface of the analyte affects a photoacoustic wave signal intensity, the signal which is generated by the irradiation light. In order to perform an inspection with high precision, it is desirable to reduce the effect by the irradiation unevenness.

Also, if an abnormal event occurs in the light source or the optical system for some reason, the abnormal state of the light output function has to be detected.

The present invention is made in light of the situations. The present invention provides a photoacoustic apparatus capable of recognizing light quantity unevenness, which occurs on a surface of an analyte, and decreasing image unevenness resulted from the light quantity unevenness.

The present invention also provides a photoacoustic apparatus capable of detecting an abnormal event with a simple configuration if the abnormal event occurs in a light source or an optical system.

Solution to Problem

According to a first aspect of the present invention, a photoacoustic apparatus includes a light source configured to irradiate an analyte with light; an optical system configured to guide the light from the light source to the analyte; a detecting unit including a receiving element configured to receive an acoustic wave that is generated in the analyte by the light; a signal processing unit configured to acquire information about the inside of the analyte from a detected signal that is acquired from the detecting unit; an optical absorber configured to absorb the light from the light source; and a calculation unit configured to calculate an irradiation intensity distribution of the light from the light source on the basis of a detected signal that is acquired when the receiving element receives the acoustic wave generated from the optical absorber.

According to a second aspect of the present invention, a photoacoustic apparatus includes a light source configured to irradiate an analyte with light; an optical system configured to guide the light from the light source to the analyte; a detecting unit including a receiving element configured to receive an acoustic wave that is generated in the analyte by the light; a signal processing unit configured to acquire information about the inside of the analyte from a detected signal that is acquired from the detecting unit; an optical absorber configured to absorb the light from the light source; and a judging unit configured to judge whether an intensity of the detected signal acquired when the receiving element receives the acoustic wave generated from the optical absorber is within a predetermined intensity range indicative of that the light source or the optical system is normal.

Advantageous Effects of Invention

With the first aspect of the present invention, the photoacoustic apparatus includes the optical absorber and the detecting unit receives the photoacoustic wave generated from the optical absorber. Accordingly, the light quantity unevenness occurring at the surface of the analyte can be recognized, and the image unevenness resulted from the light quantity unevenness can be reduced.

With the second aspect of the present invention, the photoacoustic apparatus includes the optical absorber, and the intensity of the photoacoustic wave generated from the optical absorber corresponds to the state of light irradiation. Accordingly, if a failure occurs in the light source or the optical system, the failure can be recognized with the simple configuration.

DESCRIPTION OF EMBODIMENTS

Embodiments of the present invention will be described in detail below with reference to the drawings. The same reference signs are basically applied to the same components, and the redundant description will be omitted.

First Embodiment

Photoacoustic Apparatus

Figure 1:
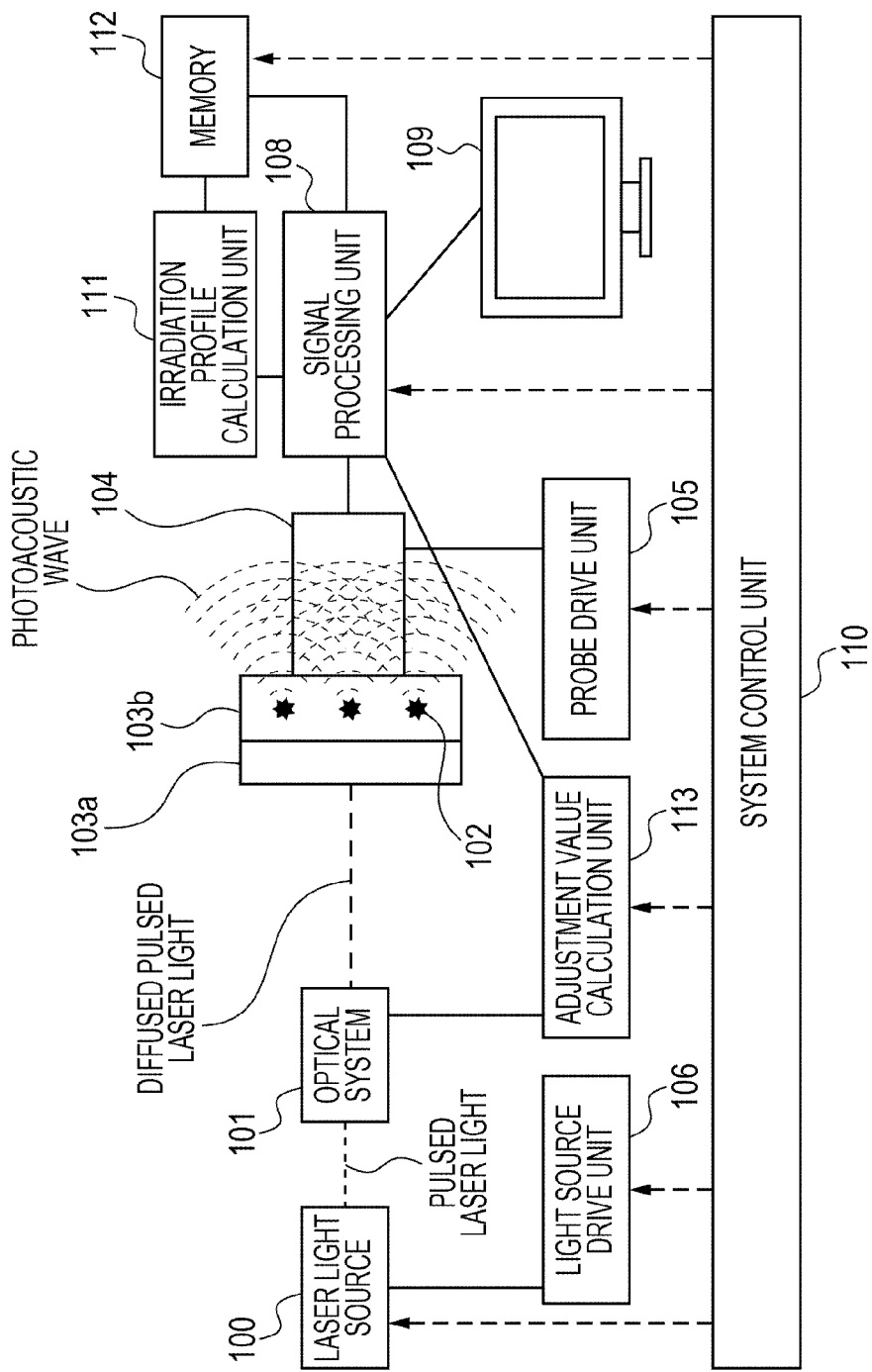
FIG. 1 is a block diagram schematically showing a configuration of a photoacoustic apparatus according to a first embodiment of the present invention.

A configuration of a photoacoustic apparatus according to a first embodiment will be described with reference to FIG. 1. The photoacoustic apparatus according to this embodiment is a photoacoustic imaging apparatus that acquires information about the inside of an analyte (in particular, forms an image of the information). If the analyte is a living body, the photoacoustic apparatus can form an image of living body information for the purpose of diagnosis of a malignant tumor or a vascular disease, or follow-up of a chemical treatment. In the present invention, the "living body information" is an acoustic-wave source distribution generated through light irradiation. In particular, the "living body information" is an initial-sound-pressure distribution in the living body; a light-energy absorption-density distribution obtained by the former distribution; or a substance density distribution of substances that form a living tissue obtained by the former two distributions. For example, the substance density distribution may be oxygen saturation.

The photoacoustic apparatus according to this embodiment includes a laser light source 100, an optical system 101, and a probe 104, as a basic hardware configuration. The laser light source 100 is a light source that irradiates the analyte with pulsed light. Now, measurement of the analyte will be described below.

The analyte (not shown), such as a living body, is fixed between plates 103a and 103b. The plates 103a and 103b face each other, and press and fix the analyte from both sides. The plates 103a and 103b are occasionally called pressure plates 103. The pulsed light from the light source is guided to a surface of the plate 103a by the optical system 101, that is, for example, a lens, a mirror, and/or an optical fiber. Hence, the pulsed light becomes diffused pulsed light and is emitted on the analyte. If part of light energy propagating through the analyte is absorbed by an optical absorber such as a blood vessel, an acoustic wave (typically, ultrasonic wave) is generated form the optical absorber due to thermal expansion. The acoustic wave is occasionally called "photoacoustic wave." That is, since the optical absorber absorbs the pulsed light, the optical absorber increases in temperature. The increase in temperature results in volumetric expansion of the optical absorber. Hence, an acoustic wave is generated. The pulsed light desirably has a certain time width that satisfies a confinement condition of heat and stress, to efficiently confine absorption energy in the optical absorber. The time width is typically in a range from about 1 to 200 nanoseconds.

The probe 104 that detects an acoustic wave corresponds to a detecting unit including a plurality of receiving elements that detect an acoustic wave. The detecting unit detects an acoustic wave generated in the analyte, and converts the acoustic wave into an electric signal (analog signal). The detected signal acquired by the detecting unit is also called "photoacoustic signal."

A signal processing unit 108 acquires information about the inside of the analyte from the photoacoustic signal. In the signal processing unit 108, a signal amplifier amplifies the photoacoustic signal acquired by the probe 104, and an A/D converter converts the signal into a photoacoustic signal as a digital signal. An image reconfiguration unit executes arithmetical processing for the digital signal to obtain three-dimensional information. Then, an image display unit 109 displays a photoacoustic image of the analyte. All elements are controlled by a system control unit 110.

Light Source

If the analyte is a living body, the light source emits light with a specific wavelength that is absorbed by a specific component included in the living body. The light source is desirably a pulsed light source that can emit pulsed light in a range from several nanoseconds to the order of several hundred nanoseconds. The light source is desirably a laser. Alternatively, a light-emitting diode may be used instead of the laser. The laser may be any of various lasers including a solid-state laser, a gas laser, a dye laser, and a semiconductor laser.

In this embodiment, the single light source is provided. However, a plurality of light sources may be used. If the plurality of light sources are used, to increase the light irradiation intensity for the living body, a plurality of light sources that oscillate light with the same wavelength may be used, or to measure a difference in optical characteristic distribution depending on wavelengths, a plurality of light sources that oscillate light with different wavelengths may be used. The light source may use a pigment that allows the wavelength of oscillated light to be changed, or the light source may be optical parametric oscillators (OPO). Accordingly, the difference in optical characteristic distribution depending on wavelengths can be measured. The use wavelength may be in a range from 700 to 1100 nm. Such wavelengths are absorbed by the living body only by a little amount. When the optical characteristic distribution of a living tissue located relatively near the surface of the living body is obtained, a wavelength range from 400 to 1600 nm, the range which is wider than the above wavelength range, may be used.

Optical System

The light emitted from the light source may propagate through an optical waveguide. Although not shown in FIG. 1, the optical waveguide may be an optical fiber. If the optical fiber is used, a plurality of optical fibers may be used for each of the light sources to guide the light to the surface of the living body. Alternatively, the light of the plurality of light sources may be guided to a single optical fiber, and the light may be guided to the living body through the single optical fiber. Still alternatively, a mirror that generally reflects light or an optical part, such as a lens that collects light, enlarges light, or changes the shape of light, may be used to guide the light. The optical part may be any part as long as a light irradiation region on the surface of the analyte is irradiated with the light emitted from the light source, in a manner with a desirable shape.

When the laser light is guided to the optical system, irradiation unevenness, in which the intensity of the laser light may be unevenly distributed, may occur in the optical waveguide. The major factor of the irradiation unevenness is, for example, speckles appearing at the surface of a reflection mirror as described above. If a plurality of mirrors are used to determine the optical waveguide, speckles may be compositely formed every time when the light is reflected by each mirror. The irradiation profile that is finally obtained may be predicted from reflection characteristics of all mirrors arranged on the waveguide. However, since the irradiation profile depends on the combination of the individual mirrors to be used, if a part is replaced for maintenance, the irradiation profile has to be calculated again. Owing to this, the method for predicting the irradiation profile results in a troublesome work for the maintenance. This is not desirable in view of operation of the apparatus.

In contrast, even if the optical fiber is used for determining the light path, as the laser light guide unit, the irradiation unevenness may occur unless the incident angle and the exit angle of the light to and from the optical fiber are precisely controlled.

Probe

The probe (detecting unit) 104 detects an acoustic wave and converts the acoustic wave into an electric signal. The photoacoustic wave generated from the living body is an ultrasonic wave with frequencies in a range from 100 KHz to 100 MHz. Hence, the probe (acoustic wave detecting unit) 104 is an ultrasonic wave detecting unit configured to receive the frequencies in the aforementioned frequency band. The acoustic wave detecting unit may be, for example, a transducer using a piezoelectric phenomenon, a transducer using an optical resonance, or a transducer using a change in capacitance, as long as the unit can detect an acoustic wave signal. The probe 104 of this embodiment may include a plurality of receiving elements that are two-dimensionally arranged. Since the two-dimensionally arranged elements are used, the acoustic wave can be detected simultaneously at a plurality of positions. The detection time can be reduced, and the influence of vibration of the analyte can be reduced. Also, an agent for acoustic impedance matching, such as gel or water, may be used between the probe 104 and the analyte to suppress reflection of the sonic wave.

Plate

The plates each desirably have a light transparency that does not reduce the photoacoustic effect provided by the diffused pulsed laser SPL, and an ultrasonic transparency that does not reduce the photoacoustic wave. Typically, the plates 103a and 103b may be made of acryl or polymethyl pentene. The plates 103a and 103b may have any thickness as long as the thickness provides an intensity that can suppress deformation of the plates 103a and 103b during holding. Typically, the plates 103a and 103b each have a thickness of about 10 mm.

Optical Absorber

The photoacoustic apparatus according to this embodiment includes an optical absorber 102 that particularly absorbs light that is emitted from the light source, as a feature of the photoacoustic apparatus. As the optical absorber 102 has a higher light absorptance, the photoacoustic wave is more efficiently generated. For example, the optical absorber 102 may be formed of a solid color substance such as graphite. If a specific analyte is present as a measurement subject, the optical absorber 102 may be made of a material that exhibits a photoacoustic characteristic obviously different from the photoacoustic characteristic of the analyte. To be more specific, if the analyte is a human body, for example, a black gel ball may be used.

Figure 2:
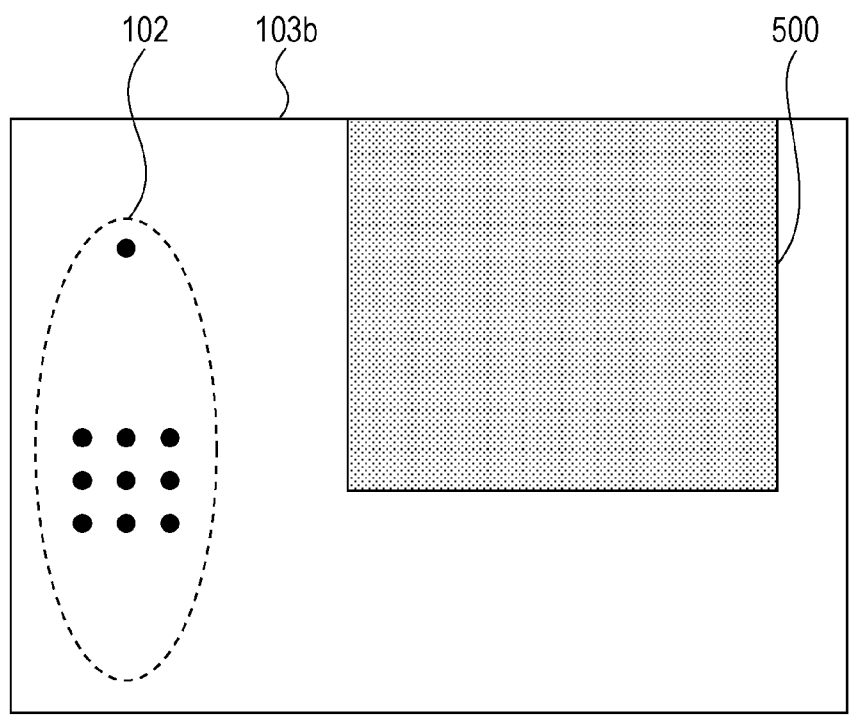
FIG. 2 illustrates an arrangement state of an optical absorber according to the first embodiment of the present invention.

To simplify the configuration of the apparatus, the optical absorber 102 may be desirably arranged in the plate 103a or 103b or on the surface of that plate. FIG. 2 illustrates an arrangement relationship between the optical absorber and a measurement region (actual measurement region 500) in which the analyte is arranged, when the plate 103b is viewed from the probe 104. Referring to FIG. 2, the optical absorber 102 with a certain size is arranged in a region other than the measurement region.

The size of the optical absorber 102 affects the frequencies of the photoacoustic wave generated from the optical absorber 102, and hence, is determined on the basis of a frequency band to be measured. In this embodiment, a fundamental frequency of a photoacoustic wave from the analyte functions as a reference. The photoacoustic wave has a feature that a signal with a large N-type waveform appears. A peak frequency Fc of the N-type waveform can be expressed as follows:

$$Fc=0.66 \times c/D,$$

where D is a diameter if the optical absorber is spherical, and c is the sound speed in the analyte. If it is assumed that the spherical optical absorber has a diameter of 1 mm, Fc is obtained such that Fc=1 MHz. A tissue (malignant tumor) to be measured has a size in a range from about 1 to 20 mm. Thus, the optical absorber 102 has a size similar to the size of the tissue. The optical absorber 102 may be desirably spherical, because the intensity, frequency, and propagation of the photoacoustic wave generated from the optical absorber 102 can be predicted through analysis.

In this embodiment, the optical absorber 102 is included in the plate 103b. Alternatively, the optical absorber 102 may be provided on the surface of the plate 103b, in the plate 103a, or on the surface of the plate 103a. Still alternatively, the optical absorbers may be provided at both the plates 103a and 103b. Yet alternatively, if the plate 103a or 103b is not provided, the optical absorber may be provided on the surface of the probe. That is, the optical absorber 102 may be located at any position in the apparatus as long as the optical absorber 102 can be irradiated with the laser light and the photoacoustic wave arrives at the probe. The laser light source 100 that irradiates the optical absorber 102 with the light is also used as the laser light source 100 for normal diagnostic measurement in this embodiment. Alternatively, different laser light sources may be used for those purposes.

Further, the optical absorber 102 may include a plurality of optical absorbers 102. This is because the irradiation intensity distribution can be calculated by an easy method, which will be described later. If the plurality of optical absorbers 102 are used, the optical absorbers 102 desirably have the same size and are desirably made of the same material.

In addition, in this embodiment, the pressure plate 103 is present between the analyte and the probe 104. In this case, a time required for the photoacoustic wave to transmit through the pressure plate 103 in the thickness direction may be a wasted time. That is, data from the time at which the laser light is emitted to the time at which the photoacoustic wave passes through the pressure plate 103 cannot be used for the reconfiguration of the diagnostic image. In other words, if the actual diagnostic measurement is carried out, the data for a predetermined period (or the time required for the photoacoustic wave to transmit through the pressure plate 103) from the time at which the laser light is emitted need not be acquired. That is, if the optical absorber 102 is present in the pressure plate 103, the photoacoustic wave from the optical absorber 102 does not adversely affect the measurement data during measurement. Accordingly, the optical absorber 102 is desirably provided at the plate 103b that is located close to the probe 104 rather than the plate 103a located close to the light source (laser light source 100).

Calculation for Irradiation Intensity Distribution

Figure 3:
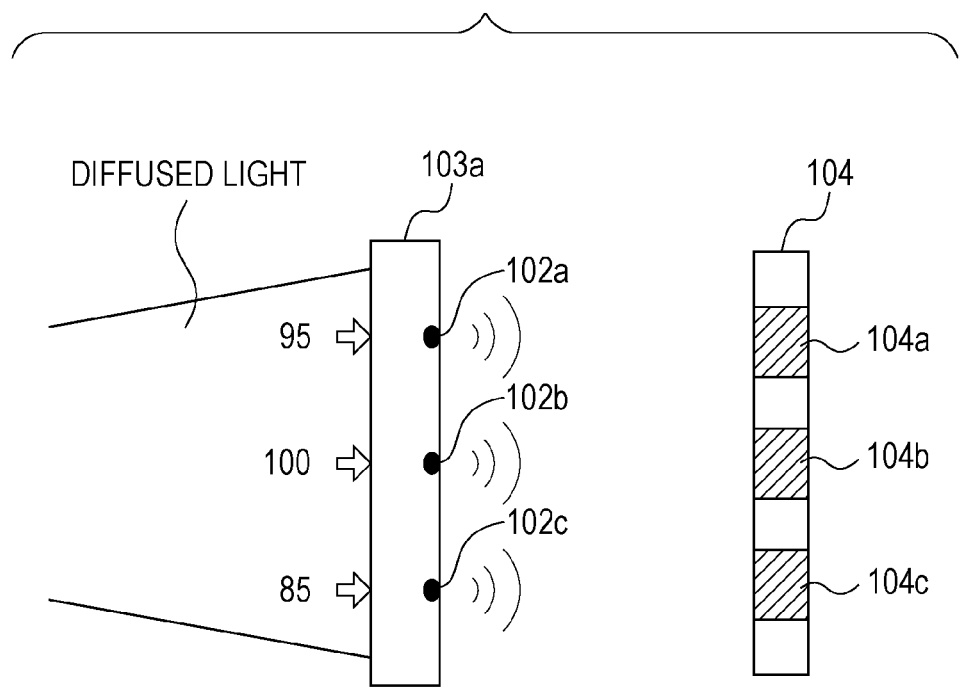
FIG. 3 schematically illustrates a calculation principle for an irradiation intensity distribution according to the first embodiment of the present invention.

Next, a process for calculating the irradiation intensity distribution of the light that is emitted from the light source while no analyte is present between the plates 103a and 103b will be described. FIG. 3 schematically illustrates a calculation principle for the irradiation intensity distribution. In this case, a plurality of optical absorbers 102a, 102b, and 102c are arranged in the plate 103a. The probe 104 including the plurality of receiving elements detects acoustic waves generated from the optical absorbers 102a, 102b, and 102c. It is assumed that the receiving elements respectively located directly below the optical absorbers 102a, 102b, and 102c are receiving elements 104a, 104b, and 104c. When the plate 103a, to which the analyte can be fixed, is irradiated with the diffused light, it is assumed that a ratio of intensities of the pulsed light that is emitted on the optical absorbers 102a, 102b, and 102c is, for example, 95:100:85. If the optical absorbers 102a, 102b, and 102c are made of the same material and have the same size, sound pressures of acoustic waves generated from the optical absorbers 102a, 102b, and 102c have the above ratio. The acoustic waves generated from the optical absorbers 102a, 102b, and 102c respectively arrive at the receiving elements 104a, 104b, and 104c, which are respectively arranged directly below the optical absorbers 102a, 102b, and 102c, at earliest timing. In this case, the acoustic waves from the optical absorbers 102a, 102b, and 102c simultaneously arrive at the receiving elements 104a, 104b, and 104c. If variation in sensitivity is not present among the receiving elements, the radio of signal intensities of the receiving elements is 95:100:85 as described above. Owing to this, if the signal processing unit 108 calculates maximum amplitudes of the received signals from the receiving elements 104a, 104b, and 104c, the light intensities of the light emitted on the optical absorbers 102a, 102b, and 102c can be obtained. Accordingly, the irradiation intensity distribution can be calculated for the three points in the light irradiation region of the plate 103a. For example, the receiving element 104b detects the acoustic wave from the optical absorber 102b and then detects the acoustic wave from the other optical absorber. In this situation, the signal intensity at early timing is used.

Herein, the plurality of optical absorbers do not have to be provided. A single optical absorber may be provided. In this case, the optical absorber may be moved to a position at which an irradiation intensity is obtained, and the signal intensity of a receiving element that is arranged directly below the optical absorber may be compared with the other signal intensity. When the light intensity distribution is measured, if the number of measurement positions is a number N within the irradiation range, the movement and light irradiation have to be carried out the N times. The movement is made by changing the position of the optical absorber relative to the position of the light irradiation region. Hence, the light source may be moved, or the optical absorber may be moved, for example, by moving the plate 103a.

As described above, the plurality of optical absorbers are desirably provided. As long as the plurality of optical absorbers are arranged to be aligned with data acquisition positions for the measurement of the irradiation profile, all elements of the probe 104 can simultaneously measure the photoacoustic waves from the plurality of optical absorbers 102. For example, if an irradiation range for profile measurement corresponds to an element range of the probe 104, the measurement can be completed only by one-time measurement.

When the optical absorbers 102 are respectively arranged above the center points of the elements of the probe 104, at positions sufficiently close to the surface of the probe, the photoacoustic wave from the optical absorber arranged above the adjacent element is incident on the target element at a large angle. The element of the probe has a directivity for reception, and has a highest sensitivity to the acoustic wave being incident perpendicularly on the element. Regarding the directivity, when the optical absorber 102 is arranged above the center point of the element, the influence of the photoacoustic wave from the adjacent optical absorber is small.

In the above description, the array transducer including the plurality of receiving elements serves as the probe 104; however, the present invention is not limited thereto. A single-element probe may be alternatively used. However, regarding the reception directivity, the probe 104 is desirably arranged directly below a single optical absorber and the photoacoustic measurement is desirably performed the number N times.

Figure 4:
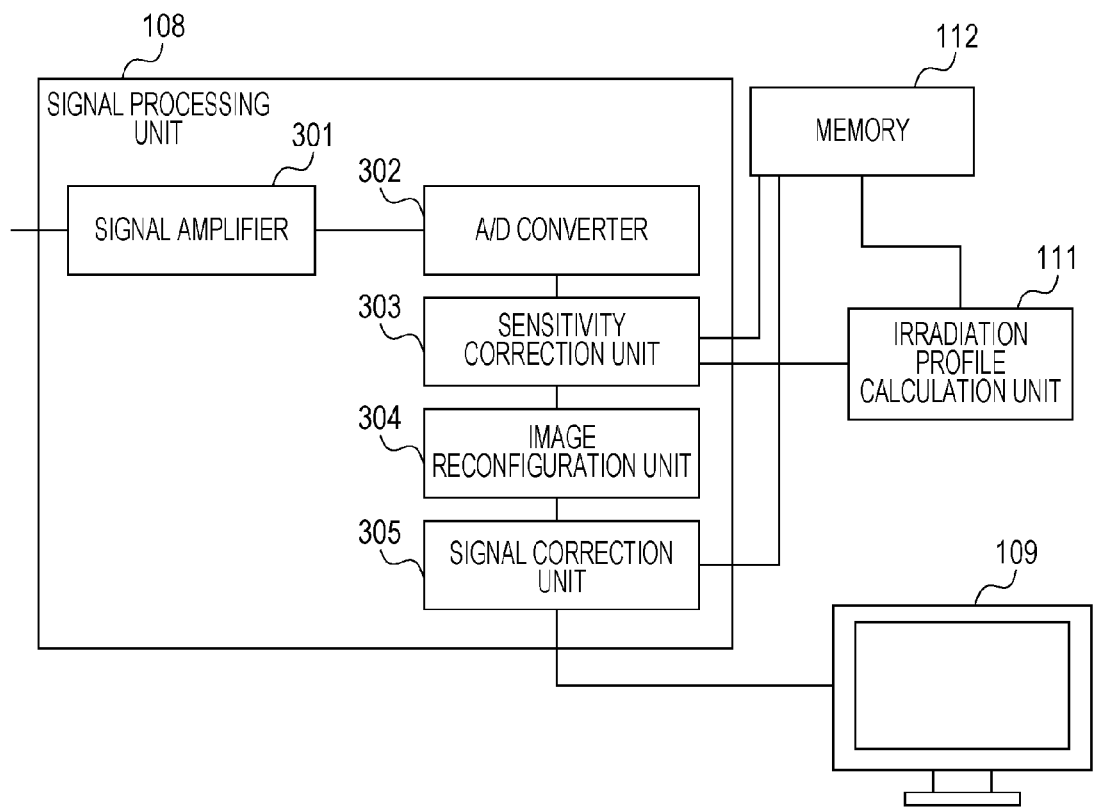
FIG. 4 is a block diagram showing an inner configuration of a signal processing unit according to the first embodiment of the present invention.
Figure 5:
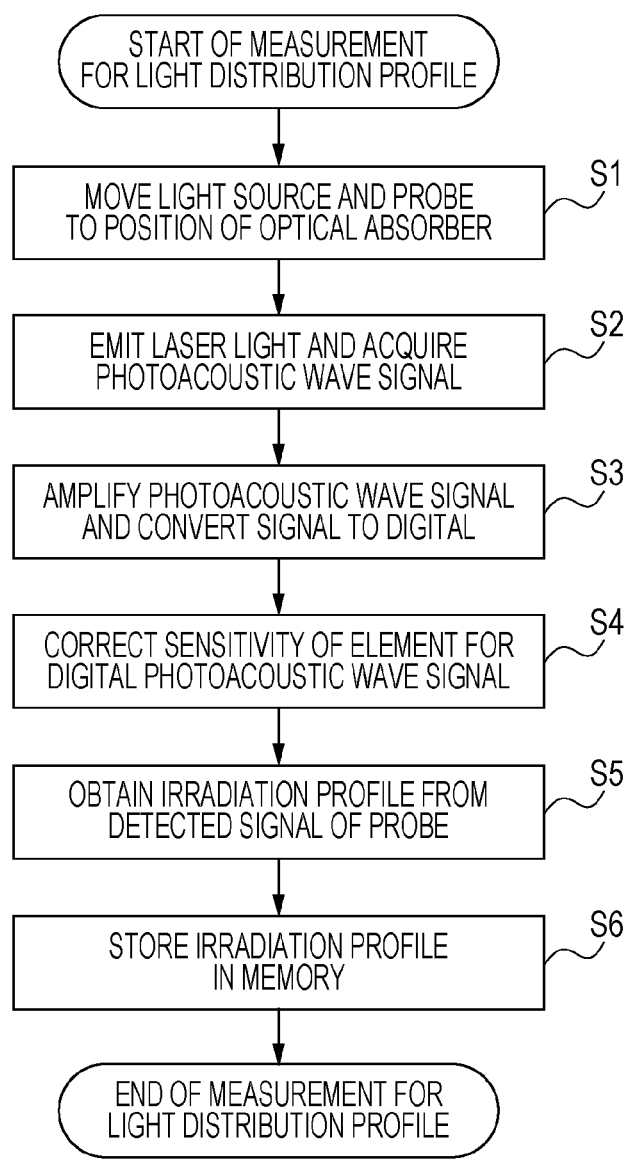
FIG. 5 is a flowchart showing a process for calculating an irradiation profile according to the first embodiment of the present invention.

FIG. 4 illustrates the signal processing unit 108 that performs signal processing for calculating the irradiation profile in the light irradiation region, from the detected signals as described above. Also, FIG. 5 is a flowchart showing an example of calculation for the irradiation profile. The signal processing unit 108 analyses a photoacoustic signal from an analyte and forms an image of the analyte even for photoacoustic measurement while the analyte is arranged.

First, the light source 100 and the probe 104 are moved to the position at which the optical absorber 102 is arranged (S1). Then, the light source 100 emits laser light, and the probe 104 receives a photoacoustic wave that is generated from the optical absorber 102 as the result of the laser light emission (S2). The photoacoustic wave received by the probe 104 is transmitted to the signal processing unit 108 as an analog photoacoustic signal that is detected by each receiving element. In the signal processing unit 108, a signal amplifier 301 amplifies the input analog photoacoustic signal, and an A/D converter 302 converts the analog signal into a digital signal (S3). If the plurality of receiving elements are provided, the signal amplifier 301 and the A/D converter 302 are provided for each element.

Then, a sensitivity correction unit 303 performs sensitivity correction for the photoacoustic signal that is converted into the digital signal (S4). This processing is performed if variation in sensitivity is present among the elements. In this embodiment, information about the variation in sensitivity among the elements of the probe 104 is stored in a memory 112. The memory 112 is a storage device, such as, a hard disk or a non-volatile memory. The sensitivity correction unit 303 corrects digital data from each element, on the basis of the information about the variation in sensitivity among the elements, the information which is stored in the memory 112.

Then, for example, by the above-described calculation method, an irradiation profile calculation unit 111 obtains an irradiation profile from the detected signal by the probe (S5). To use the irradiation profile for the photoacoustic measurement for the analyte, the irradiation profile is stored in the memory 112 (S6).

With this configuration, the light quantity unevenness appearing on the surface of the analyte can be recognized, and the image unevenness resulted from the light quantity unevenness can be reduced by a method, which will be described later.

In the description for the calculation method, when the probe includes the plurality of receiving elements, the detected signals acquired when the acoustic waves from the optical absorbers arranged directly above the receiving elements are discussed; however, the present invention is not limited thereto. For example, if the plurality of optical absorbers 102 are arranged in a known arrangement, an intensity (correct data) of a photoacoustic wave to be received by each element of the probe 104 under an irradiation condition while it is assumed that there is no irradiation unevenness can be calculated in advance. An image reconfiguration unit 304 reconfigures the digital photoacoustic signal acquired by detecting the acoustic wave from the optical absorber. Accordingly, a distribution of light absorption coefficients can be obtained. The distribution of light absorption coefficients acquired herein is information that is expressed by coordinates of the intensity of the acoustic wave generated from the optical absorber 102 and the source of the sonic wave, in the form of three-dimensional coordinates. The distribution of the light absorption coefficients is divided by the correct data and multiplied by the expected irradiation intensity. Accordingly, the intensity distribution of the irradiation light at the position of the optical absorber 102, i.e., the irradiation profile can be calculated.

Image Unevenness Reducing Method 1: Correction of Light Irradiation System

In this embodiment, an irradiation adjustment unit is desirably provided. The irradiation adjustment unit adjusts the light source or the optical system such that the distribution of the irradiation intensities is reduced on the basis of the calculated irradiation profile (the calculation result of the irradiation profile calculation unit 111). Accordingly, the pulsed light with a uniform intensity can be emitted on the surface of the analyte, and the correct information about the inside of the analyte can be acquired by the PAT measurement.

In this embodiment, an adjustment value calculation unit 113 (FIG. 1) is provided. The adjustment value calculation unit 113 calculates an adjustment value for adjustment to obtain uniform light diffusion by using the light diffusing unit on the basis of the calculated irradiation profile. If the variation exceeds a predetermined variation level, the adjustment value calculation unit 113 calculates the adjustment value, and the irradiation adjustment unit (in Method 1, the optical system 101 also serves as the irradiation adjustment unit) adjusts the degree of diffusion of the laser light.

Herein, the irradiation adjustment unit is an optical device that can correct the intensity distribution of incident light, such as a device called deformable mirror. An example of the deformable mirror may be an assembly including two piezoelectric elements bonded to each other, and the shape of the mirror can be controlled by changing a voltage in accordance with the position to which the voltage is applied. For the deformable mirror, a control matrix for driving the deformable mirror is prepared to correct the irradiation profile. A voltage is impressed successively to the elements of the deformable mirror, and the resulted change in mirror surface is successively recorded by a wavefront sensor. Accordingly, a response matrix of the irradiation profile for the drive voltage of the elements is generated. By obtaining an inverse matrix of the response matrix, the control matrix for controlling the deformable mirror for an error of the irradiation profile is obtained.

In this embodiment, the above adjustment value is an impressed voltage impressed to each element for deforming the mirror surface of the deformable mirror. An error signal vector (hereinafter, referred to as irradiation profile error signal) at the position of each element is obtained from the irradiation profile, and the vector is multiplied by the response matrix of the irradiation profile. Accordingly, an adjustment value to be fed back to the deformable mirror is obtained.

Figure 6:
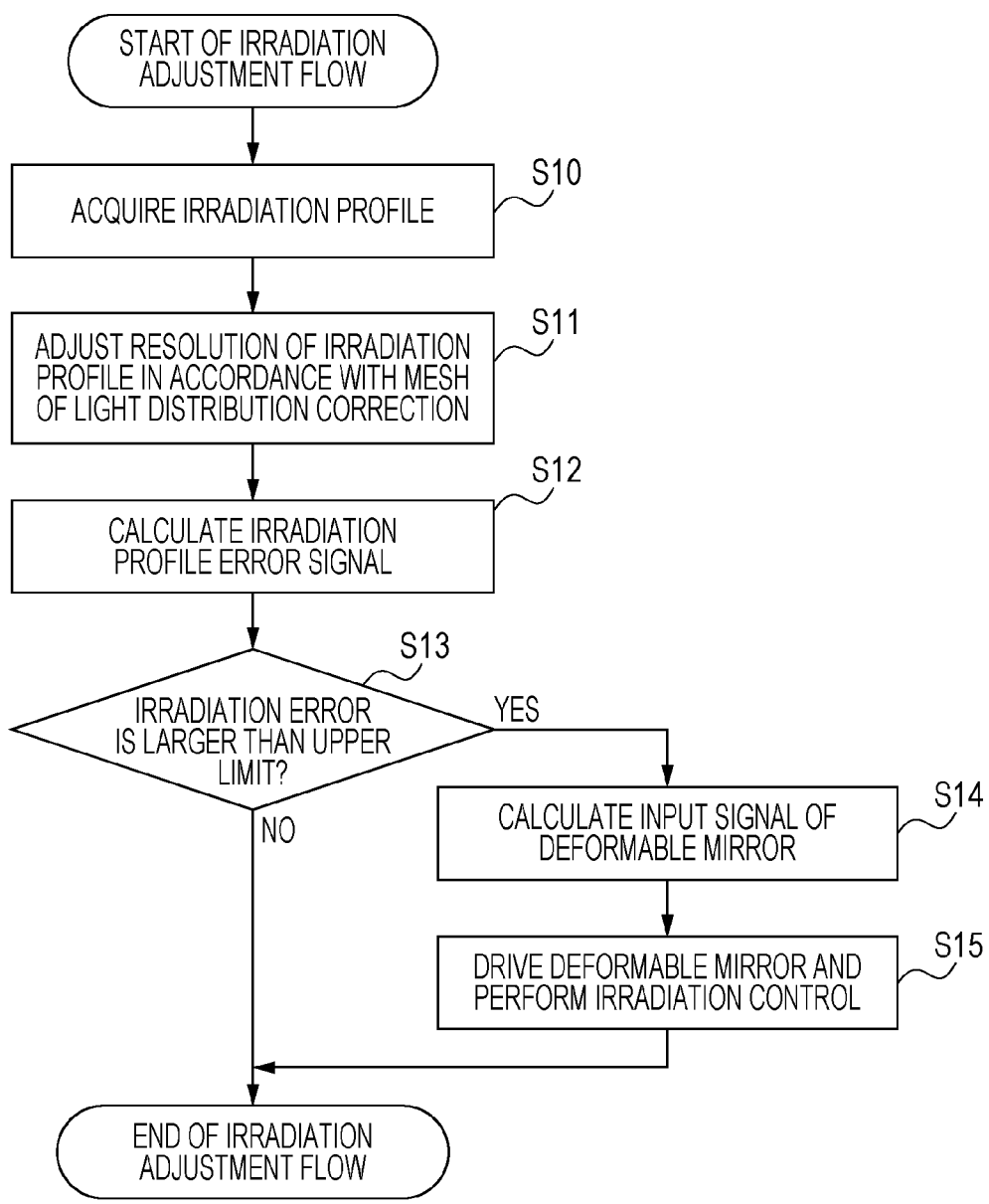
FIG. 6 is a flowchart showing a process for adjusting the irradiation profile according to the first embodiment of the present invention.

In this embodiment, the calculated irradiation profile is fed back to a deformation profile of the deformable mirror, and hence is corrected to a uniform irradiation profile. The flow of this processing will be described with reference to a flowchart in FIG. 6. In this embodiment, it is expected that the arrangement relationship between the position of a drive element for the deformable mirror and the position of the optical absorber 102 is obtained in advance. In particular, the arrangement relationship is obtained as follows.

The process for calculating the irradiation profile according to the first embodiment is performed, and the irradiation profile is acquired (S10). At this time, the light intensity at the position of the element of the deformable mirror, the position which is aligned with the position of the optical absorber 102, is expected as a corresponding irradiation profile value. The light intensity at a position other than the position which is aligned with the optical absorber 102 employs an average value that is calculated by bi-linear interpolation from the nearest irradiation profile value (S11). The ratio of the acquired irradiation profile to the average value of the irradiation profile in the entire region is calculated, and hence the irradiation profile error signal, which is calculated from the irradiation profile, is calculated (S12).

The irradiation profile error signal is compared with a certain upper limit that is determined in advance (S13). If the error exceeds the upper value, irradiation correction is performed by the following method. The irradiation profile error signal is applied to the control matrix for driving the deformable mirror, and an input signal for driving the deformable mirror is acquired (S14). The deformation control for the mirror surface is performed, and correction for bringing the irradiation profile closer to the uniform irradiation profile is performed (S15).

Image Unevenness Reducing Method 2: Correction of Detected Signal

Instead of that the optical system is corrected, the detected signal when the photoacoustic measurement is carried out for the analyte may be corrected. In particular, the signal processing unit 108 may desirably correct the detected signal when the probe (detecting unit) receives the acoustic wave generated in the analyte as the result of the light irradiation on the analyte such that variation in detected signal due to the distribution of the calculated irradiation intensities is reduced. Accordingly, even if there is the irradiation unevenness, the correct information about the inside of the analyte can be acquired by the PAT measurement while the effect of the irradiation unevenness is reduced. Also, the correction is made by processing the signal, and hence the correction does not need a device like a configuration for adjustment of the optical system. This is advantageous in view of the cost.

Figure 7:
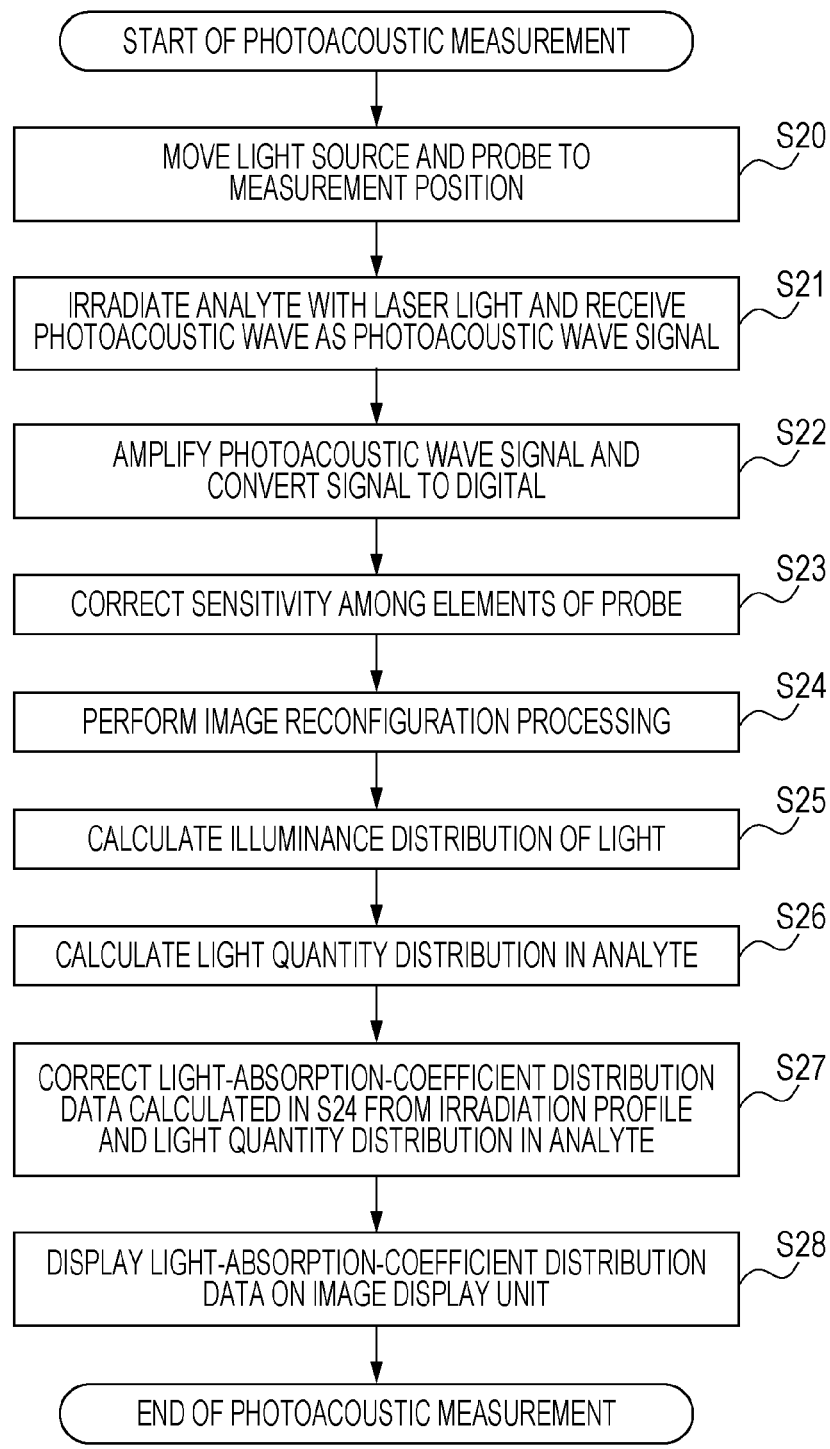
FIG. 7 is a flowchart showing a process for measuring a photoacoustic wave according to the first embodiment of the present invention.

The specific correction method will be described below with reference to flowchart in FIG. 7, together with the processing for the photoacoustic measurement of the analyte. In this embodiment, the analyte is arranged between the plates 103a and 103b and pressed and held by the plates 103a and 103b for the photoacoustic measurement. It is assumed that the analyte has a uniform surface profile because the analyte is pressed.

The laser light source 100 and the probe 104 are driven and moved to the measurement position (S20). The laser light emitted from the laser light source 100 is guided by the waveguide of the optical system 101, and propagates through the analyte. Part of the light energy propagating through the analyte is absorbed by an optical absorber, such as a blood vessel, and becomes a photoacoustic wave. The probe 104 receives the photoacoustic wave (S21). The signal amplifier 301 amplifies the photoacoustic signal, and the A/D converter 302 digitizes the analog photoacoustic signal into a digital signal (S22). Also, the sensitivities of the elements of the probe are corrected (S23). The image reconfiguration unit 304 in the signal processing unit 108 analyzes the digital data, and provides voxel data for the inside of the analyte (S24). Here, the voxel data is data obtained by dividing the inside of the analyte into small blocks (voxels) and obtaining optical characteristics, such as light absorption coefficients, respectively for the voxels. By these steps (S21 to S24), light absorptance distribution information is provisionally calculated.

In a computational space, the irradiation profile obtained by the process for calculating the irradiation profile is assumed as point sources of light in the irradiation region on the surface of the analyte. The light of the point sources is rapidly attenuated and diffused on the surface of the analyte. Assuming that the light distribution at this time is an illuminance distribution, by hypothesizing an optical coefficient of the analyte, a two-dimensional light distribution, that is, the illuminance distribution on the surface of the analyte can be obtained (S25). With the illuminance distribution and the surface shape of the analyte, a three-dimensional light quantity distribution, that is, a light quantity distribution of the light propagating through the analyte is calculated by using light diffusion equation, transport equation, or Monte Carlo light propagation simulation (S26). With the light absorption coefficient distribution and the light quantity distribution of the inside of the analyte, a photoacoustic intensity distribution of the inside of the analyte with regard to the irradiation profile can be obtained by using Expression (1) for respective corresponding positions (S27). The photoacoustic intensity distribution acquired as described above three-dimensionally expresses the light absorption coefficient distribution of the inside of the analyte. The image display unit 109 displays the distribution by a two-dimensional graphic or a three-dimensional graphic (S28). As described above, by correcting the voxel data, the image unevenness due to the irradiation unevenness can be reduced.

In this embodiment, acoustic waves from the actual measurement range that is larger than the aperture size of the probe 104 and from the optical absorber 102 arranged at a certain position are desirably measured. Owing to this, the probe 104 includes a drive unit so that the probe 104 is moved to a desirable measurement position to face an irradiation portion of the laser diffused-light source, in synchronization with the laser diffused-light source. Particularly in this embodiment, a probe drive unit 105 serves as the drive unit for the probe, and a light source drive unit 106 for driving the laser light source and the light diffusing unit (in Method 2, the optical system 101 also function as the light diffusing unit) serves as the drive unit. The drive unit for the light source does not have to move the laser light source 100 and the light diffusing unit. For example, the drive unit may only move an optical system part, such as a mirror for reflecting laser light or a tool for adjusting a light path, arranged so that the analyte or the optical absorber 102 is finally irradiated with the diffused light.

Second Embodiment

A feature of a second embodiment is that a judging unit is provided. The judging unit judges whether the intensity of the detected signal when the receiving element receives the acoustic wave generated from the optical absorber is within a predetermined intensity range indicative of that the light source or the optical system is normal.

Figure 8:
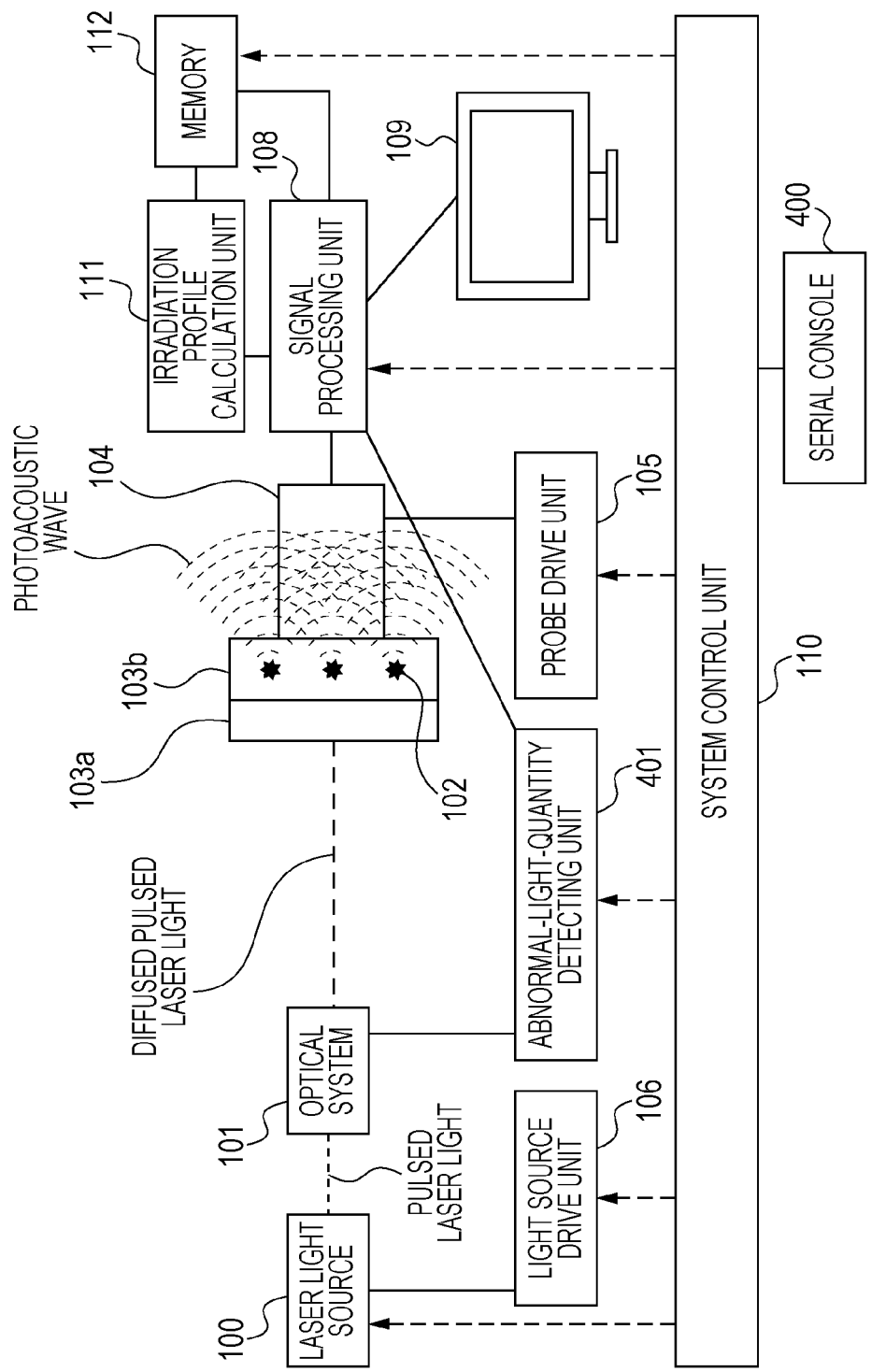
FIG. 8 is a block diagram schematically showing a configuration of a photoacoustic apparatus according to a second embodiment of the present invention.

FIG. 8 is a block diagram showing a photoacoustic apparatus according to the second embodiment of the present invention. A serial console 400 is a threshold setting unit configured to set an upper limit and a lower limit for the reception intensity of the photoacoustic wave PA. In this embodiment, the threshold setting unit is configured such that a user can set the upper limit and the lower limit for the reception intensity by a typical user interface, such as a control panel or a serial console, connected with the apparatus.

An abnormal-light-quantity detecting unit 401, which serves as the judging unit, detects an abnormal light quantity by recognizing the reception intensity of the photoacoustic wave PA as the intensity of the diffused pulsed laser light SPL. The upper and lower limits of the reception intensity designated by the user are stored in the memory 112. When the photoacoustic wave is received from the optical absorber 102, the abnormal-light-quantity detecting unit 401 references the set threshold and makes the judgment for the abnormal light quantity.

At this time, if a markedly higher intensity of the photoacoustic wave PA than expected is detected, a failure may occur in optical system parts included in the laser light source 100 and the optical system 101, or a failure may occur in the probe. Thus, if the intensity of the photoacoustic wave PA is outside the predetermined range (for example, exceeds the range), the abnormal-light-quantity detecting unit 401 detects the abnormal state. The operation is brought into an error state, and the measurement for the analyte is disabled. When the operation is shifted to the error state, the system of this embodiment limits the laser light emission control, stops the irradiation, and notifies the user about the error state. The measurement work cannot be performed until the problem is addressed by, for example, part replacement.

With this embodiment, if a failure occurs in the light source or the optical system, the failure can be detected with a simple configuration.

Third Embodiment

Figure 9:
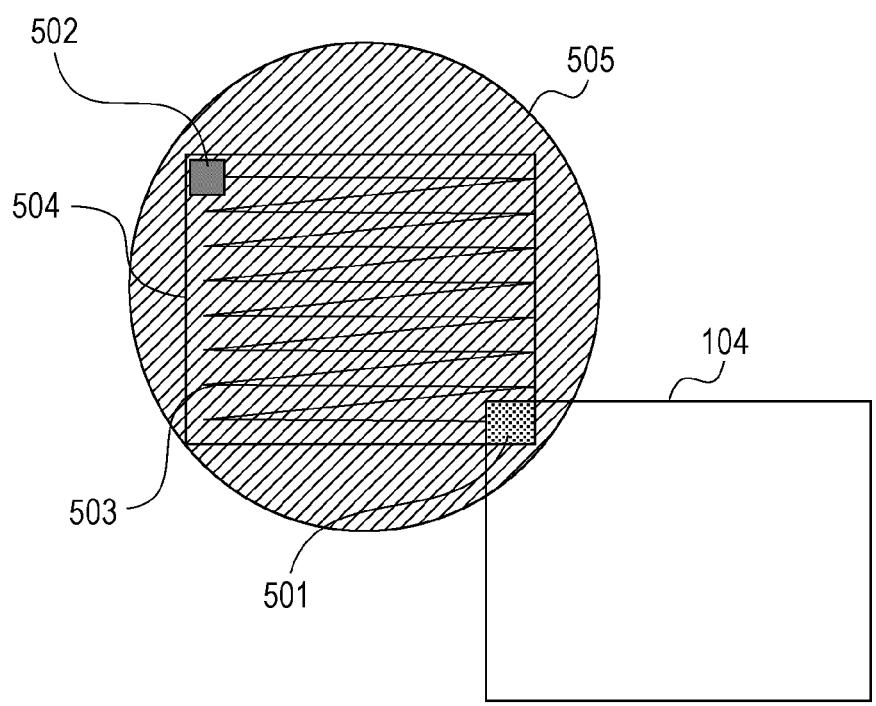
FIG. 9 illustrates a method for detecting irradiation unevenness in a photoacoustic apparatus according to a third embodiment of the present invention.

FIG. 9 briefly illustrates detection for irradiation unevenness by a photoacoustic apparatus according to a third embodiment of the present invention.

In the first and second embodiments, the system is based on the premise of that the variation in sensitivity among the elements of the probe 104 is ignorable or corrected. This embodiment provides a method of installation for detecting the diffusion unevenness of the diffused pulsed laser light SPL if the unit for correcting the variation in sensitivity among the elements of the probe is not provided, or before the variation in sensitivity among the elements of the probe is corrected.

In this embodiment, referring to FIG. 9, the photoacoustic waves PA from the optical absorber 102 and from only one of the plurality of elements of the probe 104 are measured to detect the irradiation unevenness with the diffused pulsed laser light.

FIG. 9 briefly illustrates the measurement for the irradiation unevenness in a plane parallel to the flat surface of the pressure plate when viewed from the probe 104. In this embodiment, it is assumed that a diffused light irradiation range 505 is larger than the aperture size of the element. At this time, a diffused light distribution of a smaller region than the diffused light irradiation region, i.e., a measurement region 504 is referenced. For example, an attention element 501 from among the plurality of receiving elements of the probe 104 is considered. The attention element 501 starts measurement from a measurement start point 502, and successively performs the measurement while being moved by the probe drive unit 105 along a measurement locus 503, for the measurement of distribution unevenness of the diffused light of the entire measurement region 504 for the diffused light irradiation profile.

At this time, to measure the distribution unevenness of the diffused light by the single element such as the attention element 501, the control has to be performed such that the attention element 501, the position for the measurement of the light intensity within the measurement range 504, and the optical absorber 102 are aligned in an irradiation direction. Since the optical absorber 102 is fixed by the pressure plate 103, the probe drive unit 105 and the light source drive unit 106 are controlled to attain the above-mentioned relative positional relationship of the three elements. By repeating the movement on the measurement locus 503 and the photoacoustic measurement, the photoacoustic waves in the measurement range 504 are acquired.

Photoacoustic wave signals acquired in this way are processed in a manner similar to the process for calculating the irradiation profile. Hence, the irradiation profile for the measurement range 504 is calculated.

Fourth Embodiment

The photoacoustic apparatus according to this embodiment includes a plate having a plurality of optical absorbers 102, and a movable mechanism that moves the plate so that the optical absorbers 102 are irradiated with pulsed laser light only during measurement for irradiation unevenness.

If the plurality of optical absorbers 102 are provided, as the number of optical absorbers 102 is larger, a larger number of points can be obtained for an intensity distribution by one-time measurement. However, in the case in which the plurality of optical absorbers 102 are present, if the optical absorbers 102 are arranged in a region other than the measurement region like the first embodiment, the mount area for such optical absorbers 102 has to be excessively large, resulting in an increase in size of the apparatus. To avoid this, the optical absorbers 102 are provided at the pressure plate 103 in the measurement region. In this case, the photoacoustic waves from the optical absorbers 102 are generated even during the normal diagnostic measurement. As described in the first embodiment, the photoacoustic wave from the position being sufficiently close to the probe 104 is ignorable during the actual diagnostic measurement. Also, since the photoacoustic wave coming from a position far from the receiving element of the probe 104 has a large incident angle due to the directivity of the probe 104, the photoacoustic wave less affects the measurement. However, if the number of optical absorbers 102 increases, the acoustic waves are generated by a large amount, and the effect of the acoustic waves become no longer ignorable.

Therefore, in this embodiment, a characteristic measurement plate (not shown) including the plurality of optical absorbers 102 is provided in addition to the plate 103*a* that fixes the analyte. Further, a movable mechanism (not shown) that moves the characteristic measurement plate. When the irradiation unevenness is measured, the characteristic measurement plate is moved to a position in front of the probe 104. Then, the characteristic measurement plate is moved away from the measurement region to a position at which the characteristic measurement plate is not irradiated with the laser light to prevent the unused acoustic wave from being generated.

Fifth Embodiment

Also, the present invention may be implemented by executing the following processing. In particular, the processing includes that a system or an apparatus is supplied with software (program) that provides the functions of any of the embodiments through a network or a recording medium of any kind, and a computer (or CPU, MPU, etc.) of the system or the apparatus reads and executes the program.

With the present invention, the photoacoustic measurement apparatus capable of precisely performing the photoacoustic wave measurement by reducing the effect by the irradiation unevenness of the laser light to the photoacoustic wave signal intensity can be provided. Also, to detect the irradiation unevenness of the laser light, with the present invention, the detection is enabled by using the ultrasonic probe for the photoacoustic wave measurement. That is, the irradiation unevenness can be detected with a low cost because a detection sensor does not have to be newly added.

Further, with the present invention, by detecting the abnormal intensity of the photoacoustic wave intensity, the abnormal state of the diffused light intensity can be indirectly detected and hence, a failure of the optical system part, such as the light diffusing unit, can be detected. Thus, the photoacoustic wave measurement apparatus with higher safety can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-282287, filed Dec. 11, 2009, which is hereby incorporated by reference herein in its entirety.

REFERENCE LIST 100 laser light source
101 optical system (irradiation adjustment unit, optical diffusing unit)
102 optical absorber
103 plate
104 probe
108 signal processing unit
111 irradiation profile calculation unit
400 serial console
401 abnormal-light-quantity detecting unit

The invention claimed is:

1. A photoacoustic apparatus comprising:
a light source configured to emit light;
an optical system configured to guide the light from the light source to an analyte;
a detecting unit including a receiving element configured to receive an acoustic wave that is generated in the analyte by the light;
a signal processing unit configured to acquire information about the inside of the analyte from a detected signal that is acquired from the detecting unit; and
a calculation unit configured to calculate an irradiation intensity distribution of the light from the optical system on the basis of the detected signal that is acquired when the receiving element receives acoustic wave generated from an optical absorber configured to absorb the light from the optical system.

2. The photoacoustic apparatus according to claim 1, further comprising an irradiation adjustment unit configured to adjust the light source or the optical system such that the irradiation intensity distribution is reduced on the basis of a calculation result of the calculation unit.

3. The photoacoustic apparatus according to claim 1, wherein the signal processing unit corrects the detected signal acquired when the detecting unit receives the acoustic wave generated in the analyte such that variation in the detected signal due to the calculated irradiation intensity distribution is reduced.

4. The photoacoustic apparatus according to claim 1, wherein the optical absorber includes a plurality of optical absorbers.

5. The photoacoustic apparatus according to claim 4,
wherein the detecting unit includes a plurality of receiving elements, and
wherein the plurality of optical absorbers are respectively arranged directly above center points of the receiving elements.

6. The photoacoustic apparatus according to claim 1, further comprising:
a plurality of plates configured to fix the analyte from both sides,
wherein the optical absorber is arranged in at least one of the plates or on a surface of that plate.

7. The photoacoustic apparatus according to claim 6,
wherein the plurality of plates includes a first plate and a second plate facing the first plate, and
wherein the optical absorber is arranged in the first plate or on a surface of the first plate.

8. The photoacoustic apparatus according to claim 6, wherein the optical absorber is arranged in a region of the plate provided with the optical absorber other than a measurement region for the analyte.

9. The photoacoustic apparatus according to claim 1, further comprising:
a movable plate at which the optical absorber is arranged;
wherein the plate moves to a position at which the optical absorber is not irradiated with the light when the analyte is measured.

10. A photoacoustic apparatus comprising:
a light source configured to emit light;
an optical system configured to guide the light from the light source to an analyte;
a detecting unit including a receiving element configured to receive an acoustic wave that is generated in the analyte by the light;
a signal processing unit configured to acquire information about the inside of the analyte from a detected signal that is acquired from the detecting unit; and
a judging unit configured to judge whether an intensity of the detected signal acquired when the receiving element receives an acoustic wave generated from an optical absorber configured to absorb the light from the optical system is within a predetermined intensity range indicative of that the light source or the optical system is normal.

11. The photoacoustic apparatus according to claim 10, wherein if the intensity of the detected signal acquired when the receiving element receives the acoustic wave generated from the optical absorber is outside the predetermined range, measurement for the analyte is disabled.

12. The photoacoustic apparatus according to claim 10, wherein the optical absorber includes a plurality of optical absorbers.

13. The photoacoustic apparatus according to claim 12,
wherein the detecting unit includes a plurality of receiving elements, and
wherein the plurality of optical absorbers are respectively arranged directly above center points of the receiving elements.

14. The photoacoustic apparatus according to claim 10, further comprising:
a plurality of plates configured to fix the analyte from both sides,
wherein the optical absorber is arranged in at least one of the plates or on a surface of that plate.

15. The photoacoustic apparatus according to claim 14,
wherein the plurality of plates includes a first plate and a second plate facing the first plate, and
wherein the optical absorber is arranged in the first plate or on a surface of the first plate.

16. The photoacoustic apparatus according to claim 14, wherein the optical absorber is arranged in a region of the plate provided with the optical absorber other than a measurement region for the analyte.

17. The photoacoustic apparatus according to claim 10, further comprising:
a movable plate at which the optical absorber is arranged;
wherein the plate moves to a position at which the optical absorber is not irradiated with the light when the analyte is measured.

18. A method for controlling a photoacoustic apparatus comprising the steps of:
irradiating an optical absorber that is provided in the apparatus with light;
receiving an acoustic wave that is generated from the optical absorber when the optical absorber receives the light, by a detecting unit; and
calculating an irradiation intensity distribution of the light on the basis of the detected signal that is acquired when the receiving element receives the acoustic wave generated from the optical absorber.

19. A method for controlling a photoacoustic apparatus comprising the steps of:
irradiating an optical absorber that is provided in the apparatus with light from a light source through an optical system;
receiving an acoustic wave that is generated from the optical absorber when the optical absorber receives the light, by a detecting unit; and
judging whether an intensity of a detected signal acquired when the detecting unit receives the acoustic wave generated from the optical absorber is within a predetermined intensity range indicative of that the light source or the optical system is normal.

20. A photoacoustic apparatus comprising:
a detecting unit including a receiving element configured to receive an acoustic wave that is generated when an analyte is irradiated with light;
a signal processing unit configured to acquire information about the inside of the analyte from a detected signal that is acquired from the detecting unit; and
a calculation unit configured to calculate an irradiation intensity distribution of the light on the basis of a detected signal that is acquired when the receiving element receives an acoustic wave generated from an absorber configured to absorb the light.

* * * * *